(12) United States Patent
Brisken

(10) Patent No.: US 6,361,554 B1
(45) Date of Patent: Mar. 26, 2002

(54) METHODS AND APPARATUS FOR THE SUBCUTANEOUS DELIVERY OF ACOUSTIC VIBRATIONS

(75) Inventor: Axel F. Brisken, Fremont, CA (US)

(73) Assignee: Pharmasonics, Inc., Sunnyvale, CA (US)

( * ) Notice: Subject to any disclaimer, the term of this patent is extended or adjusted under 35 U.S.C. 154(b) by 0 days.

(21) Appl. No.: 09/343,950

(22) Filed: Jun. 30, 1999

(51) Int. Cl.[7] .................................................. A61F 2/06
(52) U.S. Cl. ........................................ 623/1.1; 128/899
(58) Field of Search ................................. 604/507, 113, 604/22; 601/2; 606/108, 169; 600/504, 505; 623/1.1, 1.11, 1.12, 1.13; 128/899

(56) References Cited

U.S. PATENT DOCUMENTS

| | | | |
|---|---|---|---|
| 5,059,166 A | | 10/1991 | Fischell et al. |
| 5,078,736 A | * | 1/1992 | Behl ............................ 623/1 |
| 5,199,939 A | | 4/1993 | Dake et al. |
| 5,302,168 A | | 4/1994 | Hess |
| 5,315,998 A | | 5/1994 | Tachibana et al. |
| 5,318,014 A | | 6/1994 | Carter |
| 5,362,309 A | | 11/1994 | Carter |
| 5,443,495 A | | 8/1995 | Buscemi et al. |
| 5,487,760 A | | 1/1996 | Villafana |
| 5,616,114 A | | 4/1997 | Thornton et al. |
| 5,620,409 A | * | 4/1997 | Venuto et al. ................. 601/2 |
| 5,722,979 A | * | 3/1998 | Kusleika ...................... 606/108 |
| 5,836,896 A | * | 11/1998 | Rosenschein |
| 5,914,345 A | | 6/1999 | Slepian et al. |
| 6,015,387 A | * | 1/2000 | Schwartz et al. ........... 600/504 |
| 6,053,873 A | * | 4/2000 | Govari et al. ............... 600/505 |
| 6,070,094 A | | 5/2000 | Swanson et al. |
| 6,086,573 A | * | 7/2000 | Siegel et al. ................ 604/507 |
| 6,170,488 B1 | * | 1/2001 | Spillman, Jr. et al. ...... 128/899 |

FOREIGN PATENT DOCUMENTS

| | | | |
|---|---|---|---|
| GB | 2321853 | * 12/1998 | ................ 623/1.11 |
| WO | WO 99/35999 | 7/1999 | |

OTHER PUBLICATIONS

He et al., "Application of ultrasound energy for intracardiac ablation of arrhythmias" Eur. Heart J. (1995) 16:961–966.

* cited by examiner

Primary Examiner—David H. Willse
Assistant Examiner—Alvin Stewart
(74) Attorney, Agent, or Firm—Townsend and Townsend and Crew LLP

(57) ABSTRACT

Methods for delivering vibrational energy to subcutaneous tissue sites comprise externally generating acoustic energy and directing the external energy to an implanted structure which is capable of resonating at a pre-selected frequency. The vibration of the implanted structure, in turn, will reradiate heat and mechanical energy into tissue surrounding the structure. In one example, the implanted structure is a stent and the vibrational energy is intended to inhibit hyperplasia in a blood vessel in which the stent is implanted.

13 Claims, 3 Drawing Sheets

METHODS AND APPARATUS FOR THE SUBCUTANEOUS DELIVERY OF ACOUSTIC VIBRATIONS

BACKGROUND OF THE INVENTION

1. Field of the Invention

The present invention relates generally to medical devices and methods. More particularly, the present invention relates to methods and apparatus for enhancing and localizing the delivery of vibrational energy to internal body target sites, such as sites within the vasculature at risk of hyperplasia.

A number of percutaneous intravascular procedures have been developed for treating atherosclerotic disease in a patient's vasculature. The most successful percutaneous treatment is percutaneous transluminal angioplasty (PTA) which employs a catheter having an expansible distal end, usually in the form of an inflatable balloon, to dilate a stenotic region in the vasculature to restore adequate blood flow beyond the stenosis. Other procedures for opening stenotic regions include directional atherectomy, rotational atherectomy, laser angioplasty, and the like. While these procedures, particularly PTA, have gained wide acceptance, they continue to suffer from the subsequent occurrence of restenosis.

Restenosis refers to the re-narrowing of an artery within weeks or months following an initially successful angioplasty or other primary treatment. Restenosis afflicts up to 50% of all angioplasty patients and results at least in part from smooth muscle cell proliferation in response to the injury caused by the primary treatment, generally referred to as "hyperplasia." Blood vessels in which significant restenosis occurs will require further treatment.

A number of strategies have been proposed to treat hyperplasia and reduce restenosis. Such strategies include prolonged balloon inflation, treatment of the blood vessel with a heated balloon, treatment of the blood vessel with radiation, the administration of anti-thrombotic drugs following the primary treatment, stenting of the region following the primary treatment, and the like. While enjoying different levels of success, no one of these procedures has proven to be entirely successful in treating all occurrences of restenosis and hyperplasia.

Of particular interest to the present invention, the use of stents has shown great promise for the reduction of restenosis, particularly in the time period immediately after angioplasty or other primary interventional treatment. Even the use of stents, however, is subject to hyperplasia where the lumen defined by the stent becomes occluded, typically within months following the stent placement.

For that reason, the inhibition of hyperplasia following stent placement has become an area of significant research and commercial effort. For example, it has been proposed to expose a stented region within the vasculature to radiation from radioisotopes in order to inhibit hyperplasia. While initial data appear promising, the need to employ radioisotopes is problematic for the patient, the treating staff, and the hospital which must maintain and dispose of the radioisotopes. As an improvement over the use of radioisotopes, the use of catheters for delivering ultrasonic energy to an angioplasty and/or stent placement site has also been proposed. See, U.S. Pat. No. 5,836,896, and copending application Ser. No. 09/223,230. The latter is commonly assigned with the present application, and its full disclosure is incorporated herein by reference.

While the delivery of radiation, ultrasonic energy, and possibly other forms of energy, by catheter immediately following angioplasty, stent implantation or other interventional procedures appears to be at least partially effective, it has been noted that hyperplastic activity reaches a peak several days following the initial intervention. Thus, ameliorative treatment immediately following the initial intervention may be ill-timed. It is possible that treatment delayed by one or more days after the initial intervention would be more effective. Moreover, it may be desirable to treat the interventional site multiple times following the interventional procedure, possibly over a period of days, weeks, or even months. The need to reintroduce a treatment catheter, however, makes such delayed and repetitive treatment much less feasible.

For these reasons, it would be desirable to provide alternative and improved methods and apparatus for the treatment and inhibition of hyperplasia in blood vessels following placement of a stent or other vascular prosthesis. It would be particularly desirable to provide methods and apparatus for the delivery of acoustic or vibrational energy to a target site within the vasculature or elsewhere where a stent, graft, or other device has been previously implanted. Such methods and apparatus should permit non-invasive delivery of the acoustic energy to the target site and preferably facilitate localization of the energy at the target site. Such methods and apparatus should be suitable for treatment of the vasculature, particularly following placement of a stent or other vascular prosthesis, and should also find use in virtually any situation where an artificial structure has been implanted at a target site within the patient's body.

2. Description of the Background Art

U.S. Pat. No. 5,836,896, and copending application Ser. No. 09/223,230, have been described above. Intravascular inhibition of hyperplasia by exposure to radioisotopes is described in a number of patents and publications, including U.S. Pat. Nos. 5,616,114; 5,302,168; 5,199,939; and 5,059,166. The therapeutic application of ultrasonic energy is described in a number of patents and publications including U.S. Pat. Nos. 5,362,309; 5,318,014; 5,315,998; and others. A high frequency ultrasonic catheter employing an air-backed transducer is described in He et al. (1995) Eur. Heart J. 16:961–966.

SUMMARY OF THE INVENTION

The present invention provides methods and apparatus for non-invasive delivery of vibrational energy to target sites within a patient's body. The target sites will be defined by the prior implantation of a structure having pre-selected mechanical characteristics which allow at least a portion of the structure to resonate when excited by externally applied acoustic energy. In the exemplary embodiment, the implanted structure is a stent (as defined below), but it could also be a vascular graft, filter, valve, or other type of structure which is known to be implanted within the vasculature for therapeutic or diagnostic purposes. In all cases, the structure will be modified to resonate at a pre-selected frequency when the structure is exposed to externally applied acoustic energy at a suitable excitation frequency. In addition to vascular structures, the methods of the present invention are suitable for use with a variety of non-vascular implanted structures where it is desired to deliver and localize vibrational energy to a subcutaneous target site. For example, resonant structures may be implanted at or near tumor sites in order to localize and facilitate the delivery of vibrational energy to such sites, typically to induce heating and hyperthermic treatment of the site.

In the case of stents and other vascular structures, the purpose of the treatment will usually be to inhibit hyperplasia, most usually inhibiting hyperplasia within a stent or vascular graft. In the case of stents, the materials, geometries, and other design features will be selected to allow at least a portion of the stent, typically the entire stent, to resonate at a relatively low frequency, typically from 5 kHz to 500 kHz, preferably from 50 kHz to 100 kHz. The frequency, power, duty cycle, and other characteristics of the acoustic energy being delivered from an external source to the stent will be selected to be compatible with the stent characteristics. Typically, the excitation frequency will be within the range from 5 kHz to 500 kHz, preferably from 50 kHz to 100 kHz, while the intensity level (spatial peak temporal average; SPTA) measured at the tissue surface through which the energy is being delivered will be in the range from 0.01 W/cm$^2$ to 1000 W/cm$^2$, preferably from 0.5 W/cm$^2$ to 50 W/cm$^2$. The acoustic energy may be applied continuously, i.e., with a 100% duty cycle, or discontinuously, e.g., with a duty cycle in the range from 5% to 95%, usually from 10% to 50%. Reradiated power levels will be below those applied at the skin surface but will be precisely located at the site where hyperplasia may occur.

In the case of vascular treatments, it is believed that the vibrational energy reduces hyperplasia within the implanted stent or other prosthesis by inducing cellular apoptosis, direct inhibition of cell proliferation, direct initiation of a healing response, or some combination of these mechanisms. Regardless of the actual mechanism, the methods and systems of the present invention will be clinically effective in reducing or in at least some cases substantially eliminating hyperplasia associated with primary vascular treatments and secondary implantation of the stent or other implantable structure.

Once the structure has been implanted, acoustic energy may be delivered to resonate the structure at almost any time, beginning immediately after the implantation and continuing for an unlimited time thereafter. In the case of vascular hyperplasia inhibition, it is believed that treatment should be repeated at least one and preferably more times beginning one or more days after the initial stent implantation. It will of course be possible to treat the region immediately following implantation (and in some cases using intravascular catheters substantially at the time of implantation), but it is a particular advantage of the present invention that treatments can be carried out in the days, weeks, and months following implantation without the need to regain intravascular access. It is presently preferred that subsequent treatments be performed at least once during the period from 1 day to 30 days following the initial implantation, more preferably being at least once during the period from 1 day to 7 days following the initial implantation. Treatments at a greater frequency and/or before and after these preferred treatment times may also be of significant benefit.

In a first aspect, a method according to the present invention for inhibiting hyperplasia at a site in a patient's vasculature, comprises generating acoustic energy externally to the patient. The generated energy is directed to a site where a prosthesis, such as a stent or vascular graft, has previously been implanted. The acoustic energy is delivered under conditions which cause at least a portion of the prosthesis to resonate and to reradiate vibrational energy into the blood vessel wall surrounding the stent. The vibrational energy will be delivered in an amount and for a time sufficient to inhibit hyperplasia. Typically, the reradiated vibrational intensity (SPTA) will be at a level in the range from 0.001 W/cm$^2$ to 100 W/cm$^2$, preferably 5 W/cm$^2$ to 50 W/cm$^2$. Treatment times may be in the range from 5 seconds to 10 minutes, preferably from 30 seconds to 5 minutes. While at least one treatment will be performed, preferably during the periods noted above, it will be possible to repeat the treatments much more frequently, typically at intervals from 6 hours to 28 days, preferably from 1 day to 7 days.

In a second aspect, methods according to the present invention comprise generating acoustic energy external to the patient and directing the acoustic energy to an implanted structure at a subcutaneous body site, either vascular or non-vascular. The energy is delivered at a frequency which causes the implanted structure to resonate and reradiate vibrational energy into the tissue surrounding the implanted structure. The frequencies will typically be in the range from 5 kHz to 500 kHz, preferably from 50 kHz to 100 kHz, and the intensity (SPTA) delivered at a site on the patient's skin through which the energy is directed will be typically be in the range from 0.001 W/cm$^2$ to 1000 W/cm$^2$, preferably from 0.5 W/cm$^2$ to 50 W/cm$^2$.

The present invention still further comprises subcutaneously implantable structures, where the structures have a pre-selected resonant frequency which allows the structure when implanted to be resonantly excited by an externally generated acoustic energy which is directed at the structure. Preferably, the structures will be in the form of stents, vascular grafts, or other structures intended for vascular implantation. Such structures may be designed to have resonant characteristics within the ranges set forth above by incorporating and distributing appropriate masses and spring characteristics about the structure.

The present invention still further comprises kits including a stent or vascular graft or other implantable structure at least a portion of which is configured to resonate at a resonant frequency in the range from 5 kHz to 500 kHz. The kits will further include instructions for directing acoustic energy in the range from 5 kHz to 500 kHz at the structure after implantation. Instructions may optionally further set forth that the acoustic energy is to be directed at the structure at a time from 1 day to 30 days after implantation.

DESCRIPTION OF THE SPECIFIC EMBODIMENTS

Figure 1:
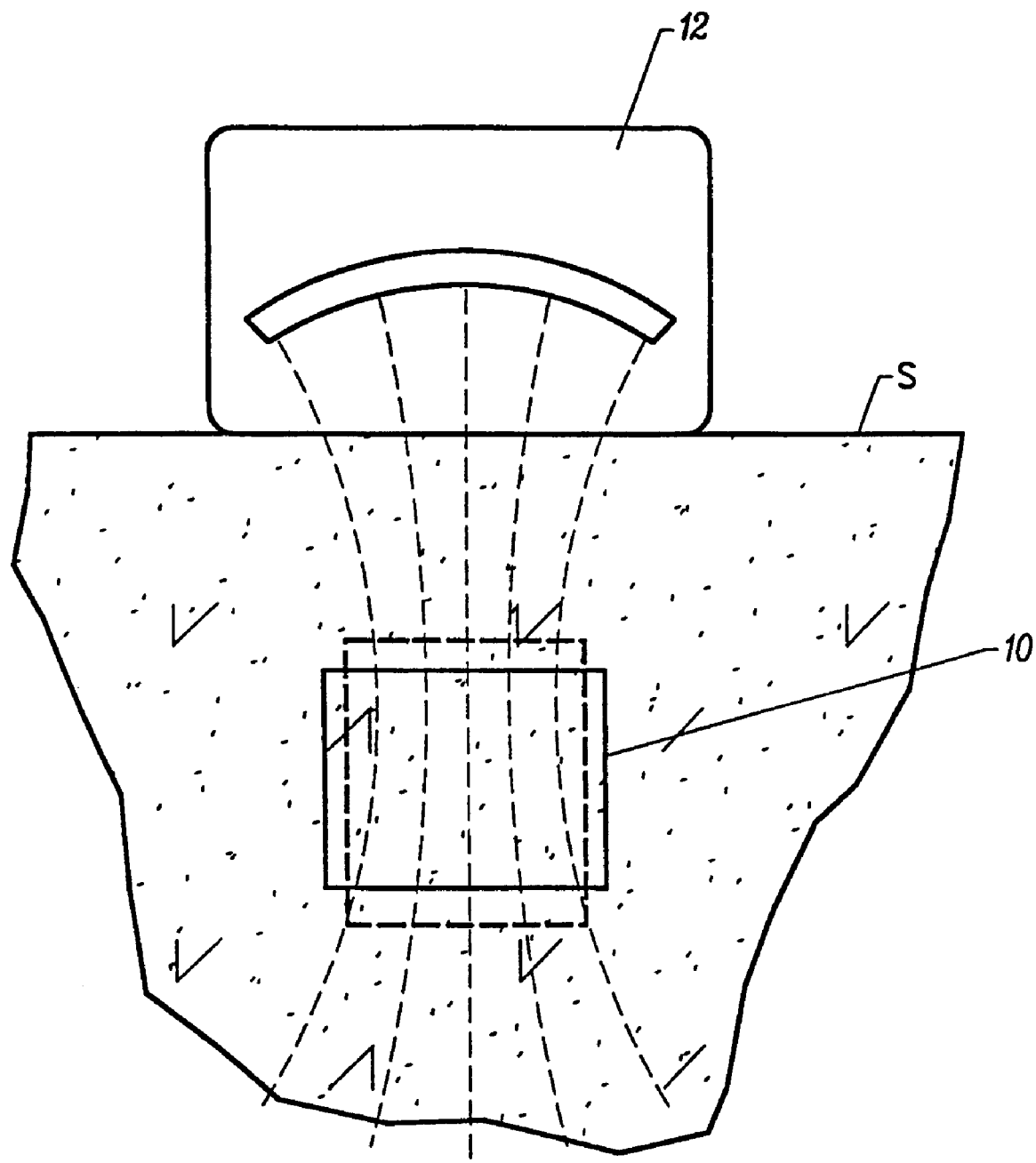
FIG. 1 is a schematic illustration of an implanted structure being resonantly excited by the application of acoustic energy from an external source according to the methods of the present invention.

Referring to FIG. 1, an implantable structure 10 is located subcutaneously beneath the surface S of a patient's body. An acoustic transducer 12, typically a large aperture ultrasonic transducer, is positioned externally on the outer body surface at a location over the implanted device 10. Preferably, there will be a direct line between the acoustic energy source 12 and the implanted device 10 which is free from regions of the body which will not efficiently transmit acoustic energy, such as the lungs and the bones. The acoustic transmitter 12 is then energized to deliver acoustic energy to the site of the implanted structure 10, typically having a focussed beam which is aimed at the site. The aperture of the focussed beam should not be too small, however, to help assure that sufficient energy bathes the target site in order to resonantly excite the structure 10. As a result of the energy, the implanted structure 10 will begin to resonate at its resonant frequency and reradiate vibrational energy into the tissue or region immediately surrounding the device 10.

Figure 2:
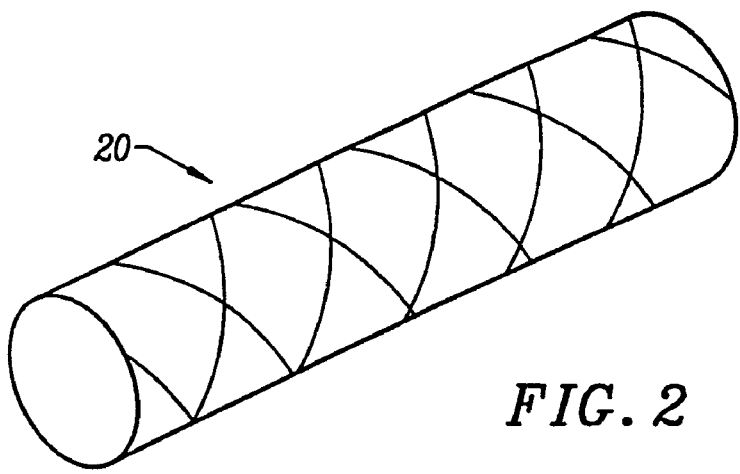
FIG. 2 illustrates an exemplary implantable structure which has been modified to have resonant characteristics in the form of an implantable stent.

A preferred implantable structure is a stent 20 illustrated in FIG. 2. The stent may be plastically deformable, self-expanding, and have virtually any of the configurations which are widely taught in the medical and patent literature. At least a portion of the stent or other implantable structure, however, will be modified or configured so that it is capable of vibrating at a resonant frequency in response to excitation from the externally generated acoustic energy. The modified portion may be integral with the stent structure or may be a separate structure coupled or joined to the implantable structure.

Figure 3:
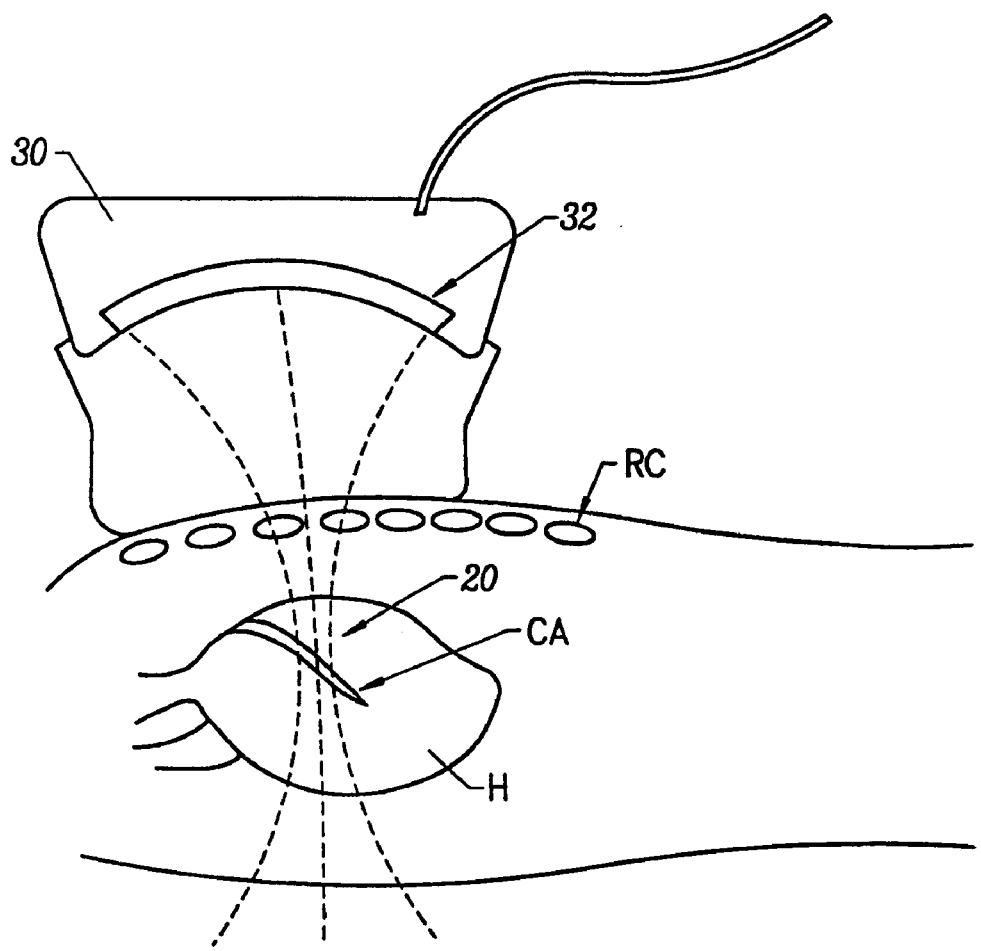
FIG. 3 illustrates a method for applying acoustic energy from an external source to resonant an implanted stent to inhibit hyperplasia according to the methods of the present invention.

Referring now to FIG. 3, the stent 20 may be implanted within a coronary artery CA of a heart H, typically following angioplasty or other primary interventional treatment. Once the stent 20 has been implanted, acoustic energy may be delivered to the stent using an acoustic energy source 30, typically including an ultrasonic transducer array 32 which is configured to focus ultrasonic energy at a distance in the range from 2 cm to 15 cm below the device so that energy is focused at the level of the heart when the device is placed on the patient's chest. Acoustic energy in the ranges set forth above will be able to penetrate between the ribs of the rib cage RC, but will generally be unable to penetrate through the lungs. Thus, the acoustic transmitter 30 should be positioned so that energy can reach the stent location without passing through a lung. Treatment times, powers, and duty cycles, have been set forth previously.

A particularly suitable acoustic generator which may be used in the methods of the present invention is described in copending application Ser. No. 09/345,661 (filed the same day as this application) the full disclosure of which is incorporated by reference.

Figure 4:
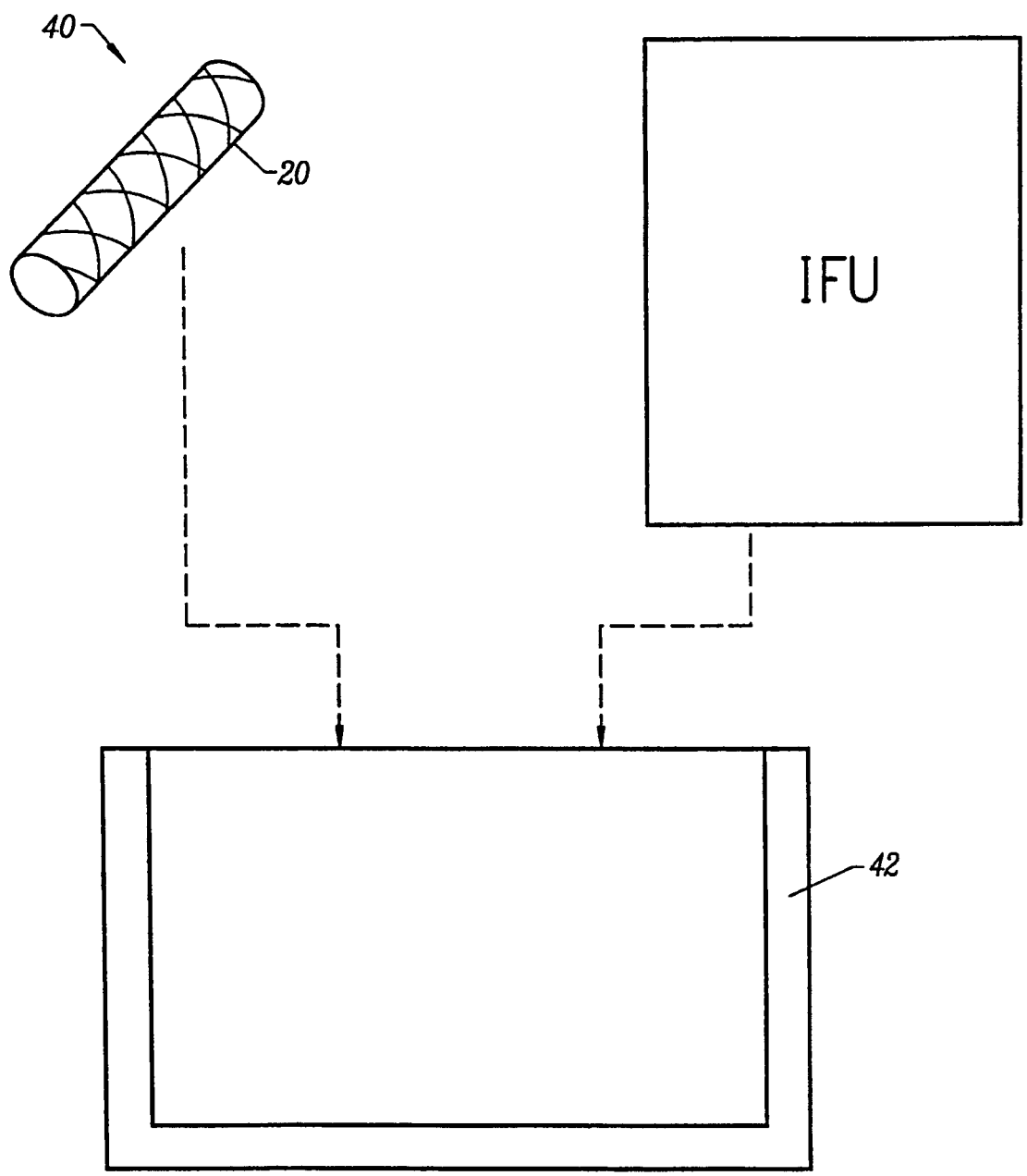
FIG. 4 illustrates a kit comprising a resonant stent together with instructions for use according to the methods of the present invention.

Referring now to FIG. 4, kits 40 according to the present invention will comprise at least an implantable device, such as stent 20, which has been modified to resonate for use in the methods of the present invention. The kits 40 will further include instructions for use IFU setting forth the methods of the present invention for resonantly exciting the implanted structure after implantation. The implantable structure and instructions for use will typically be combined together in a kit in a conventional package 42, such as a pouch, tray, tube, box, or various combinations thereof. At least the implantable structure will typically be sterilized and maintained in a sterile condition within the package. The stent 20 or other implantable device may then be implanted at a target site according to well known techniques. The novel methods of the present invention for resonantly exciting the implantable structure may then be utilized in accordance with the instructions in the IFU.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for inhibiting hyperplasia at a site in a patient's vasculature where a prosthesis has been implanted, said method comprising:

generating acoustic energy externally of the patient; and directing the acoustic energy to the prosthesis, wherein the energy is delivered prior to substantial hyperplasia under conditions which cause at least a portion of the prosthesis to resonate and reradiate vibrational energy in an amount and for a time sufficient to inhibit hyperplasia.

2. A method as in claim 1, wherein the prosthesis is a stent or a graft.

3. A method as in claim 1, wherein the acoustic energy is directed at the prosthesis at a time from 1 day to 30 days after implantation of the prosthesis.

4. A method as in claim 3, wherein the acoustic energy is directed at the prosthesis at a time from 1 day to 7 days after implantation of the prosthesis.

5. A method as in claim 1, wherein the acoustic energy is applied immediately following implantation.

6. A method as in claim 1, wherein the acoustic energy is generated at a frequency in the range from 5 kHz to 500 kHz.

7. A method as in claim 1, wherein the acoustic energy has an intensity (SPTA) in the range from 0.01 W/cm$^2$ to 1000 W/cm$^2$ at a site on the patient's skin through which the energy is directed.

8. A method for inhibiting hyperplasia by delivering vibrational energy to a subcutaneous body site of a patient, said method comprising:

generating acoustic energy external to the patient; and directing the acoustic energy to an implanted structure at said subcutaneous body site, wherein the energy is delivered prior to substantial hyperplasia at a frequency which causes the implanted structure to inhibiting hyperplasia to resonate and reradiate vibrational energy into tissue surrounding the implanted structure.

9. A method as in claim 8, wherein the acoustic energy is generated at a frequency in the range from 5 kHz to 500 kHz.

10. A method as in claim 9, wherein the acoustic energy has an intensity (SPTA) in the range from 0.01 W/cm$^2$ to 1000 W/cm$^2$ at a site on the patient's skin through which the energy is directed.

11. A method as in claim 8, wherein the implanted structure comprises a stent or a graft.

12. A kit comprising:

a stent or vascular graft structure having a resonant frequency in the range from 5 kHz to 500 kHz; and instructions for directing acoustic energy in the range from 5 kHz to 500 kHz at the structure after implantation for the treatment of vascular hyperplasia.

13. A kit as in claim 14, wherein the instructions set forth that the acoustic energy is to be directed at the structure at a time from 1 day to 30 days after implantation.

* * * * *